United States Patent
Prince et al.

(10) Patent No.: US 6,762,335 B1
(45) Date of Patent: Jul. 13, 2004

(54) APPARATUS FOR DEHYDROGENATION OF ETHYLBENZENE TO STYRENE

(75) Inventors: Kelli E. Prince, Baton Rouge, LA (US); Marcus E. Ledoux, Baton Rouge, LA (US); Honn Tudor, Baton Rouge, LA (US); L. Mark Gremillion, Baton Rouge, LA (US)

(73) Assignee: Fina Technology, Inc., Houston, TX (US)

( * ) Notice: Subject to any disclaimer, the term of this patent is extended or adjusted under 35 U.S.C. 154(b) by 0 days.

(21) Appl. No.: 09/515,314

(22) Filed: Feb. 29, 2000

(51) Int. Cl.$^7$ .............................. C07C 5/32; B01J 8/02
(52) U.S. Cl. ................ 585/440; 585/921; 585/922; 422/218; 422/220
(58) Field of Search ................ 585/440, 921, 585/922; 422/218, 220

(56) References Cited

U.S. PATENT DOCUMENTS

| | | | |
|---|---|---|---|
| 4,318,894 A | 3/1982 | Hensel et al. ............... | 423/212 |
| 4,471,821 A | 9/1984 | Coulon et al. ............... | 141/286 |
| 5,006,131 A | 4/1991 | Karafian et al. ............ | 422/201 |
| 5,133,502 A | 7/1992 | Bendig et al. .............. | 239/504 |
| 5,358,698 A | 10/1994 | Butler et al. ............... | 422/218 |
| 5,866,737 A | 2/1999 | Hagemeyer et al. ........ | 585/443 |
| 6,096,937 A | 8/2000 | Butler et al. ................ | 585/440 |

FOREIGN PATENT DOCUMENTS

| | | |
|---|---|---|
| DE | 2306516 | 8/1974 |
| EP | 0724906 | 8/1996 |

OTHER PUBLICATIONS

English Language Translation of German Patent Document 2306516 published on Aug. 14, 1974.*

* cited by examiner

*Primary Examiner*—Walter D. Griffin
(74) *Attorney, Agent, or Firm*—Bradley A. Misley

(57) ABSTRACT

The present invention discloses a process and apparatus for improving the catalyst life and efficiency in a gas flow catalyst bed reactor assembly. The reactor comprises an outer reaction vessel, an inner displacement cylinder, and an annular catalyst bed surrounding the displacement cylinder having a top half and a bottom half. Fluid flow improvement is achieved by adding at least one baffle to the top half of the displacement cylinder to improve uniformity of fluid flow in the reaction vessel and across the catalyst bed. Also disclosed is a process for improving fluid flow uniformity in a gas phase reactor comprising an outer reaction vessel, an inner displacement vessel having a top half and a bottom half and a reaction outer surface and an inert inner space, and an annular catalyst bed. The process comprises conducting fluid flow simulations using actual reactor conditions. During simulation, baffles are added on the outer reaction surface of the displacement reactor to improve simulated fluid flow. The baffles are added to the displacement cylinder by entering the inner inert space of the cylinder and attaching the baffles to the reaction outer surface from the inner inert space. The process allows the modification of existing reactors without disassembling the reactor.

3 Claims, 2 Drawing Sheets

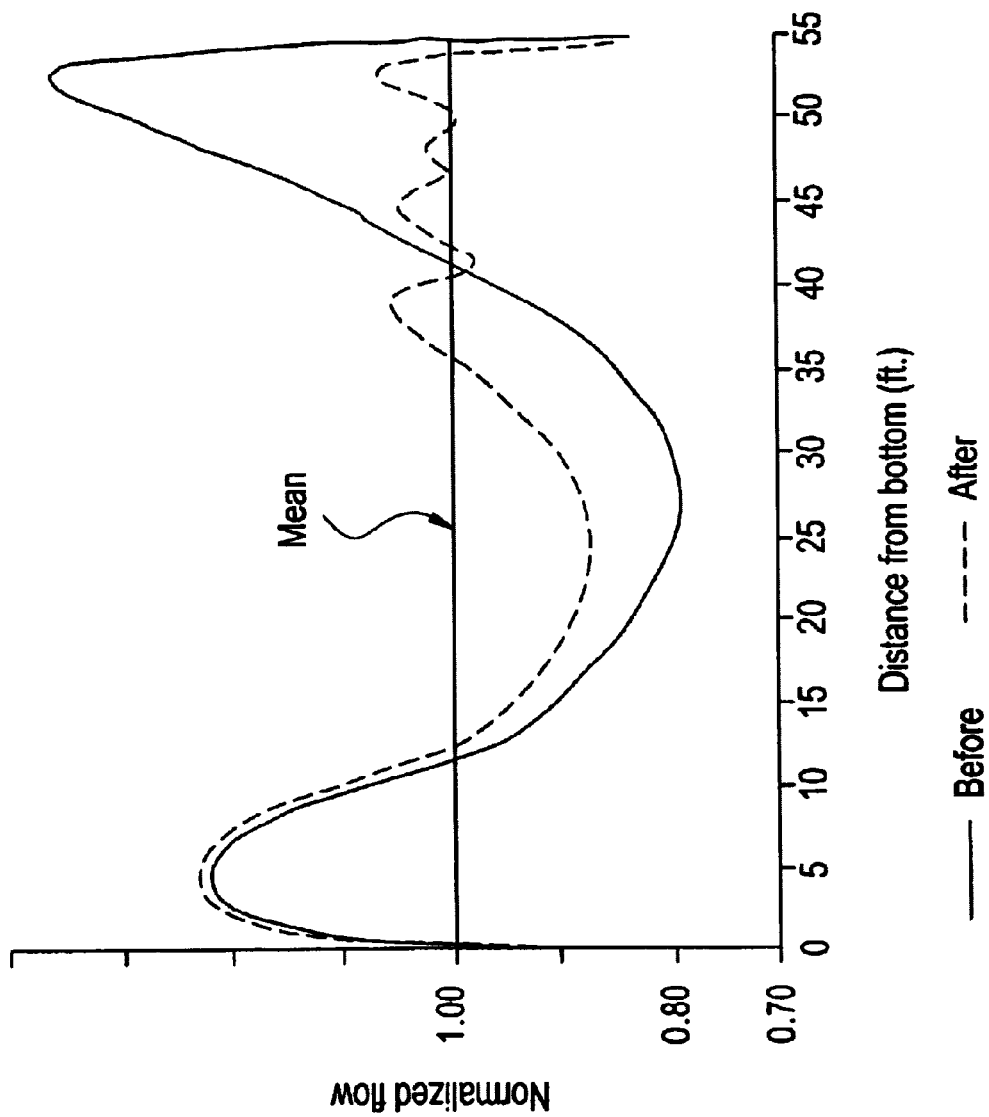

APPARATUS FOR DEHYDROGENATION OF ETHYLBENZENE TO STYRENE

BACKGROUND OF THE INVENTION

This invention relates to the field of styrene manufacture and more particularly discloses apparatus including reactor vessels for the dehydrogenation of ethylbenzene into styrene monomer.

It is well known in the art of styrene manufacture to react ethylbenzene over a dehydrogenation catalyst such as iron oxide under elevated temperatures in the range of around 1000° F. and at a pressure of about 10 to 20 PSIA in order to strip hydrogen from the ethyl radical on the benzene ring to form the styrene molecule. This is normally done in a styrene radial reactor which also is commonly termed an EB dehydro reactor. The dehydro reactors generally are elongated cylindrical vertical structures of a very large size ranging in diameter from about five to thirty feet or more and in length from about ten to one hundred feet or more. The normal construction for such a reactor allows for input of the ethylbenzene gas at an inlet located in the bottom center of the vertical reactor, whereupon the gas is flowed up through an annular area, passing radially outward through a porous catalyst bed of iron oxide or other suitable dehydro catalyst, and then passing upward through an outer annular area to exit at the top of the reactor shell. Since the flow of ethylbenzene across the catalyst bed is in a radial direction, these reactors are sometimes identified as "radial" reactors.

Normally a radial reactor would be sized such that the annular flow area inside the catalyst bed would have some relative proportional value with respect to the cross-sectional flow area of the inlet pipe delivering ethylbenzene to the reactor. Preferably the annular flow area inside the catalyst bed would be larger than the cross-sectional flow area of the flow inlet pipe. Because of the extended vertical length of such reactors, normally the inlet pipe to the bottom of the reactor must come in at a relatively sharp ninety-degree radius and the resulting effect is a side-to-side maldistribution of flow across the reactor vessel. Ideally, the inlet pipe to the reactor would be a straight vertical pipe for a considerable distance prior to entering the reactor, but due to physical configurations, this is not possible because of the extended vertical height of the reactor.

Also, due to the nature of flow across the extended vertical length of the reactors, switching from longitudinal or axial flow into radial or transverse flow and then back into longitudinal flow, flow velocities across the catalyst bed from top to bottom vary widely in conventional reactor vessels, thus resulting in degraded catalyst life in those areas of the reactor with the greatest flow velocities. It has been found by experimentation and flow velocity measurements that the highest feed velocity across the catalyst beds in a radial reactor generally occurs near the top of the reactor, and the lowest velocity across the catalyst bed occurs near the bottom of the reactor near the inlet pipe. This increased velocity at the top of the catalyst bed and reduced velocity at the bottom of the catalyst bed results in a greatly shortened life of the catalyst near the top of the reactor and forces a shutdown of the reactor for catalyst regeneration much sooner than normally desirable.

Accordingly, it is desirable to improve the flow in the reactor both in the axial and vertical directions. U.S. Pat. No. 5,358,698 to Butler et al. issued on Oct. 25, 1994 and is assigned to Fina Technology, Inc. This '698 patent discloses a method for improving the flow in a dehydrogenation reactor by using a displacement cylinder. The disclosure of this patent is hereby incorporated by reference in its entirety. While improvement in fluid flow is achieved by the method taught in the '698 patent, further improvements were needed in order to improve the efficiency of the catalyst.

SUMMARY OF THE INVENTION

The present invention discloses a dehydrogenation reactor vessel apparatus that comprises a displacement cylinder and utilizes specific baffling on the exterior of such displacement cylinder to reduce the vertical flow differences across the reactor height. The baffles are attached to the displacement cylinder without having to disassemble the reactor. The baffles are attached to the exterior of the displacement cylinder at specific locations to reduce the flow rate in the higher flow rate regions of the reactor. In one embodiment, at least two baffles are added to the top half of the reactor to allow more uniform fluid flow through the reactor.

In accordance with one embodiment of the present invention, an existing ethylbenzene dehydrogenation reactor is retrofitted to improve fluid flow and extend catalyst life. Retrofitting the reactor starts with analysis of existing reactor condition and catalyst loading. The fluid flow through the reactor is simulated. Once simulated conditions reflect actual operations, fluid flow improvements are simulated. The improvements comprise adding baffles to the displacement column at locations exhibiting higher fluid flow velocities. The location, size and number of baffles are determined by simulation to provide as uniform a fluid flow as possible. After simulation, the actual baffles are added to the outside of the displacement column without disassembly of the reactor. The baffles are preferably added to the top half of the reactor and do not extend more than half the distance from the displacement reactor to the inner wall of the catalyst bed. The process results in optimization of pressure drop while minimizing the same.

BRIEF DESCRIPTION OF THE DRAWINGS

FIG. 2 shows the normalization of fluid flow in one reactor modified in accordance with the present invention.

DETAILED DESCRIPTION

Figure 1:
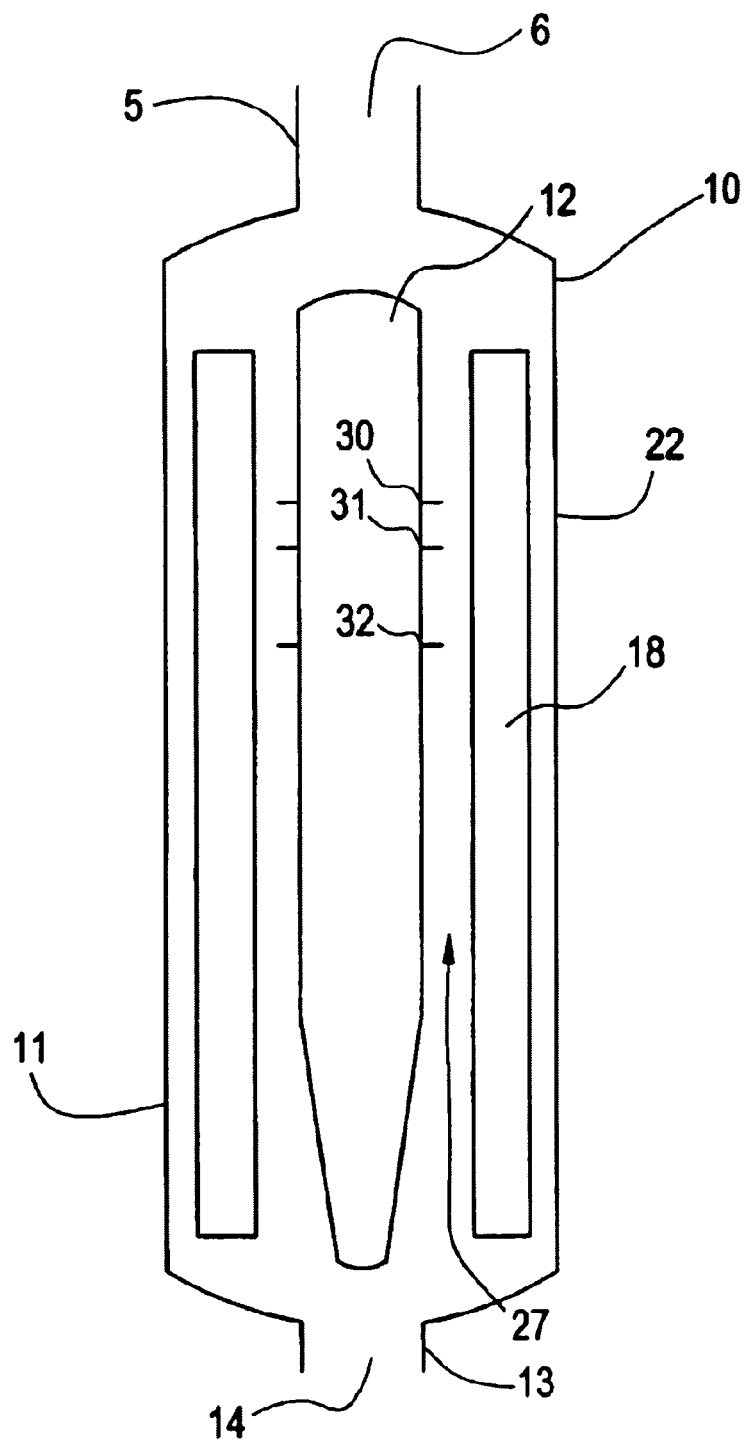
FIG. 1 illustrates a cross sectional schematic diagram of the reactor vessel and baffles location in accordance with one embodiment of the present invention.

As has been the trend in the industry, larger reactors for the manufacture of styrene are utilized in order to reduce operating costs. While the present invention is described relative to an ethylbenzene dehydrogenation reactor to form styrene, the invention is applicable to improving the operations of large reactors with fixed catalyst beds.

FIG. 1 is a schematic cross sectional side view of an EB dehydro reactor vessel 10 having an elongated outer cylindrical shell 11 enclosing an inner cylindrical displacement member 12 located concentrically inside cylindrical vessel 11. Vessel 11 and displacement member 12 are generally right circular cylinders, meaning that a cross sectional view taken perpendicular to the longitudinal center lines of these two vessels would be circular in shape. Preferably, displacement cylinder 12 is located co-axially within vessel 11, meaning that the central longitudinal axis of the two cylindrical structures coincide. An inlet pipe 13 having a large cross sectional area is connected to a central inlet opening 14 formed in the bottom of shell 11. Preferably inlet pipe 13 is also cylindrical in cross sectional area.

The placement of cylinder 12 within vessel 10 in a coaxial alignment serves to form an annular catalyst area 18 around the displacement cylinder. A series of optional radially outwardly extending flow baffles may be formed on the outer wall of catalyst bed, extending radially outward therefrom to further direct flow of gases flowing through the catalyst bed and directing them into a radial flow direction, thereby preventing longitudinal flow and further smoothing out flow across the catalyst bed. Once these catalyst bed baffles are installed, the locations cannot be changed without long downtime and disassembly of the reactor.

The catalyst bed 18 comprises a concentric cylindrical catalyst shell made of a perforated or porous inner wall and a similar porous or perforated outer wall. Preferably, the catalyst shell is sufficient to maximize flow and still retain the dehydro catalyst between the inner and outer walls. Some typical catalysts utilized in the dehydrogenation process are those sold by United Catalyst (Styromax series) and by Criterion (such as Versicat series). These may be of the iron oxide type or other dehydrogenation types of catalysts. The shape and size of the catalyst particles varies and may have an effect on the fluid flow in the reactor.

The sizing of the flow areas of the inlet pipe 13 and the annular area 21 (inner annulus) between the displacement cylinder 12 and the catalyst bed 18 is preferably in the range of about 2 to 1 with annular area 21 being approximately twice the value of the cross sectional area of pipe 13. Furthermore, the annular area 22 (outer annulus) between catalyst bed 18 and vessel 11 is relatively narrow and would not allow sufficient space for later modifications or work in the area. To perform any work on the interior of the vessel wall 11, the catalyst bed 18 must be removed. This represents significant cost and long downtime. Outlet pipe 5 and opening 6 provide the means for removal of product from the reactor. Baffles 30, 31, and 32 are shown in accordance with one embodiment of the present invention. These baffles affect the flow through the reactor and do not operate to achieve the same function of any baffles that may be present in the inlet pipe 13 or baffles on catalyst trays.

The present invention is particularly suitable for the modification of existing reactors as can be seen from the following discussion. For an existing reactor, a steady state flow simulation is conducted in accordance with well known methods. In one embodiment, a cold flow is conducted using a two-dimensional axis-symmetric reactor model. The geometry is divided into about 14,000 hexahedral cells. Average values for temperature, molecular weight and specific heats were utilized from actual historical data at the affected plant. Table 1 below shows typical operating conditions.

TABLE 1

| Flow, lb./h | 500,000 |
| Exit pressure, psia | 8–14 |
| Average temperature, ° F. | >1000 |
| Average molecular weight | 25.9–26.2 |
| Average viscosity, cp | 0.003 |
| Average specific heat, J/Kg. ° C. | 2400–2500 |

Catalyst bed porosity was also considered. This took into account the shape and particle size of the catalyst. Various catalysts were considered, including smooth, shaped and ribbed versions. Catalyst pellet diameter ranged from 3–3.5 millimeters (mm) with pellet length from 4–9 mm. The catalyst bed densities varied from 70 to 95 pounds per cubic foot. The catalyst bed porosity changes during reactor operations, achieving its lowest value at end-of-run operation.

The velocity profile and pressure was calculated for each cell within the reactor geometry. Calculations for fluid flow simulations are well known in the art and the methods to achieve such are not subject of this invention.

Flow distribution for a reactor similar to that shown in FIG. 1, but without baffles 30, 31 and 32, showed that the top 20% and the bottom 20% of the reactor bed operated at higher than normal LHSV. On the other hand, the middle 60% operated at lower than normal LHSV. Thus, flow as a function of distance decreased in the bottom half of the reactor and increased in the top half of the reactor. The increase in the flow in the top half is attributed to the higher pressure drop in the outer annulus as compared to that in the inner annulus. At the bottom half, the increased flow was attributed to excessive inner annulus pressure drop as compared to the outer annulus.

It was determined that for a retrofitting of an existing reactor, the best approach to correct the fluid flow was to place baffles of specified size at specific heights on the displacement cylinder to provide as close to uniform flow through the reactor. Adding rings or baffles in the top section of the inner annulus increased, the inner annulus pressure drop to match the pressure drop in the outer annulus. Catalyst bed fluidization was taken into account in the placement and number of baffles or rings. Some of the requirements of the present invention include the optimization of pressure drop in addition to minimization of pressure drop. In other words, the addition of baffles increases the pressure drop in the reactor. The addition of the baffles should be done with minimal increase in pressure drop and maximum effect on fluid flow normalization. Additionally, it is preferred that the baffles extension into the reactor is limited to not exceed half the distance from the outer wall on the displacement cylinder to the inner wall of the catalyst bed, i.e., half the width of the inner annulus. This combination of factors is included in the simulation solution for fluid flow normalization.

The addition of baffles or rings on the outer surface of the displacement cylinder (cylinder 12) allows the modification of the reactor fluid flow without having to take out the displacement cylinder or the catalyst trays or structure. The displacement cylinder is of sufficient width that a man way is cut into the top and work is performed from the inside of the displacement cylinder. The cylinder wall is cut at the required location and the baffles are added and welded from the inside. This does not require any dismantling of the reactor and the changes can be made with minimum down time.

In accordance with one embodiment of the present invention, an existing ethylbenzene dehydrogenation reactor was analyzed and modified. The reactor space was 62 feet in height with a 60 inch diameter inlet and an 88 inch diameter outlet. The reactor had an inside diameter of 13.5 feet. The outside diameter of the displacement cylinder was 5.75 feet. The catalyst bed had an inner diameter of 7 feet and 5.25 inches and an outer diameter of 12.5 feet. The reactor had an outer annulus of 6 inches depth. In operation, this reactor had a flow rate of over 500,000 pounds per hour. As can be seen from the dimensions, the available space inside the reactor does not allow room for individuals to work in the available space. Any modification to the system would require dismantling of the reactor. This has been the case until the present invention. To improve the fluid flow of this reactor according to its operating parameters, three baffles or rings were installed on the outer surface (reaction side) of the displacement reactor. The baffles are shown as items 30, 31 and 32 in FIG. 1. The top ring 30 was installed at a height of 49 feet and extended 7.5 inches into the reactor. The middle ring or baffle 31 was installed at a height of 46.75 feet and extended 6.25 inches into the reactor. The bottom ring 32 was installed at a height of 40 feet and extended 5.0 inches into the reactor. These baffles resulted in a more uniform flow of fluid through the reactor. As can be seen, the baffles were added to the top half of this reactor with increasing extension to the reactor as height in the reactor is increased. The improvement in the fluid flow uniformity resulted in increased catalyst life and efficiency.

FIG. 2 shows the effect of adding the baffles in the above example. The solid line shows the fluid flow in the vertical direction through the reactor prior to the addition of the baffles. The graph shows the above normal fluid flow at the lower part of the reactor and the top part. The addition of the baffles resulted in normalizing the flow at the top (location of the baffles) and improving fluid flow through the middle.

Thus, the present invention, as disclosed in the aforementioned drawings and descriptions corresponding thereto, provides means and apparatus for the dehydrogenation of ethylbenzene to styrene, which process and apparatus enjoys the advantages of extended catalyst life and closer control of flow velocities at various points up-and-down the reactor cross-sectional configuration. Conventional reactors suffer from short catalyst life due to non-consistent flow velocities across varying sections of the catalyst beds.

It was also discovered that flow velocities through the top of the catalyst bed were in the range of one and one-half to two and one-half times higher than those across the middle of the bed. Thus, it was realized that utilization of the catalyst in the reactor was far from uniform, which in turn contributed directly to much shorter than expected catalyst life.

As a result, the present invention discloses reactor configurations that significantly reduce the vertical flow velocity variations. This is achieved by the use of baffles along the exterior wall of the displacement reactor. Flow simulations are utilized to determine the number, location and size of the baffles.

In typical operation, ethylbenzene feedstock is supplied to the reactor vessels via feed supply line 13 through inlet area 14. From there the feed material flows into the reactor around the catalyst beds 18. Operating conditions in the reactor are preferably in the range of about 900° to 1225° F. temperature, and about 8–22 PSIA pressure. Flow velocities in the reactor range from about 100 to 400 fps, with a preferred overall flow velocity through the reactor of around 200 to 300 fps.

Although certain preferred embodiments of the present invention have been herein described in order to provide an understanding of the general principles of the invention, it will be appreciated that various changes and innovations can be effected in the described dehydrogenation reactor assembly without departing from these principles. For example, whereas the preferred embodiment is described as adding three baffles at the top half of the reactor, the number and location of the baffles may vary depending on the particular reactor. Also, it is apparent that different baffling shapes could be utilized to achieve flow normalization. Other changes would be apparent to one skilled in the art and therefore the invention is declared to cover all changes and modifications of the specific examples of the invention, herein disclosed for purposes of illustration, which do not constitute departures from the spirit and scope of the invention.

What is claimed is:

1. A process for improving fluid flow uniformity in a gas phase reactor comprising an outer reaction vessel, and inner displacement cylinder having a top half and a bottom half and a reaction outer surface and an inert inner space, and an annular catalyst bed, the process comprising:

conducting fluid flow simulations using actual reactor conditions;

adding baffles on the outer reaction surface of the displacement cylinder to improve simulated fluid flow; and adding the baffles to the displacement cylinder by entering the inner inert space of the cylinder and attaching the baffles to the reaction outer surface from the inner inert space.

2. The process of claim 1 wherein three baffles are added to the top half of the displacement cylinder and wherein said baffles are added without disaddembly of the reactor or catalyst bed.

3. The process of claim 1 wherein the annular catalyst bed is at a certain distance from the displacement cylinder and wherein the baffles extend into the reaction vessel by a distance not greater than half the distance to the catalyst bed.

* * * * *